US006270757B1

(12) United States Patent
Warne

(10) Patent No.: US 6,270,757 B1
(45) Date of Patent: Aug. 7, 2001

(54) FORMULATIONS FOR IL-11

(75) Inventor: Nicholas W. Warne, Methuen, MA (US)

(73) Assignee: Genetics Institute, Inc., Cambridge, MA (US)

( * ) Notice: Subject to any disclaimer, the term of this patent is extended or adjusted under 35 U.S.C. 154(b) by 0 days.

(21) Appl. No.: 08/230,982

(22) Filed: Apr. 21, 1994

(51) Int. Cl.$^7$ .................................................... A61K 38/20
(52) U.S. Cl. .......................................... 424/85.2; 530/351
(58) Field of Search .............................. 424/85.2; 530/351

(56) References Cited

U.S. PATENT DOCUMENTS

| | | | |
|---|---|---|---|
| 4,496,537 | * 1/1985 | Kwan | 424/85 |
| 4,675,183 | * 6/1987 | Kato et al. | 424/85.1 |
| 4,774,091 | * 9/1988 | Yamahira et al. | 424/426 |
| 5,215,743 | * 6/1993 | Singh et al. | 424/85.1 |
| 5,215,895 | * 6/1993 | Bennett et al. | 435/69.52 |
| 5,236,704 | * 8/1993 | Fujioka et al. | 424/85.1 |
| 5,270,181 | 12/1993 | McCoy et al. | 435/69.7 |
| 5,292,646 | 3/1994 | McCoy et al. | 435/69.7 |
| 5,358,708 | * 10/1994 | Patel | 424/85.1 |
| 5,371,193 | * 12/1994 | Bennett et al. | 530/351 |

FOREIGN PATENT DOCUMENTS

| | | | |
|---|---|---|---|
| 0 158 487 A2 | 10/1985 | (EP) | A61K/37/02 |
| 0 578 823 A1 | 1/1994 | (EP) | A61K/47/42 |
| WO 94/05318 A1 | 3/1994 | (WO) | A61K/37/02 |

OTHER PUBLICATIONS

Pikal, Bio Pharm vol. 3, No. 9, pp 26–30, Oct. 1990.*
Cherel et al., Blood, vol. 86(7), pp 2534–2540, 1995.*
Kopf et al., Nature, vol. 368(6469) pp 339–342, 1994.*
Neben et al., Stem Cell (Dayt), vol. 11 Suppl. 2, pp 156–162, Jul. 1993.*
Sinkai et al., Jour. Interferon Res., vol. 13 (Suppl. 1), p. S77, 1993.*
Hamblin, Cytokines and Cytokine Receptors, IRL Press, pp. 10, 15, 34, 1993.*
Paul et al., PNAS, vol. 87, pp. 7512–7516, 1990.*
Wang et al., J. of Pareteral Sci. & Tech., vol. 42(25), pp. S3–A26, 1988.*
Manning, et al., Pharmaceutical Research 6:903–918 (1989).

* cited by examiner

Primary Examiner—Chhaya D. Sayala
(74) Attorney, Agent, or Firm—Ivor R. Elrifi; Mintz Levin

(57) ABSTRACT

The present invention provides novel formulations comprising IL-11 and glycine. Also provided are compositions, both liquid and lyophilized, comprising IL-11 and glycine and optionally, a buffering agent such as histidine and phosphate.

20 Claims, No Drawings

FORMULATIONS FOR IL-11

FIELD OF INVENTION

The present invention relates to novel formulations comprising IL-11

BACKGROUND OF THE INVENTION

A variety of regulatory molecules, known as cytokines, have been identified including interleukin-11 (IL-11). IL-11 stimulates a variety of hematopoietic and immune functions. The various protein forms of IL-11 and DNA encoding various forms of IL-11 activity are described in Bennett, et al., U.S. Pat. No. 5,215,895 (June 1, 1993); McCoy, et al., U.S. Pat. No. 5,270,181 (Dec. 14, 1993); and McCoy, et al., U.S. Pat. No. 5,292,646 (Mar. 8, 1994), and incorporated herein by reference. Thus, the term "IL-11" includes protein produced by recombinant genetic engineering techniques; purified from cell sources producing the factor naturally or upon induction with other factors; or synthesized by chemical techniques; or a combination of the foregoing.

To maximize the pharmacological benefit of any protein, it is essential to have finished dosage forms that are stable, easily and reproducibly manufactured, and designed for standard routes of administration. Specifically, it is desirable to have stable, concentrated forms of bulk protein, e.g., IL-11 which, in turn, are suitable for further manufacture of finished dosage forms of protein, which can then be administered e.g., via sub cutaneous injection.

In both bulk protein and finished dosage forms, protein stability can be affected by such factors as ionic strength, pH, temperature, repeated cycles of freeze/thaw and shear forces. Active protein may be lost as a result of physical instabilities, including denaturation and aggregation (both soluble and insoluble aggregate formation), as well as chemical instabilities, including, for example, hydrolysis, deamidation, and oxidation, to name just a few. For a general review of stability of protein pharmaceuticals, see, for example, Manning, et al., Pharmaceutical Research 6:903–918 (1989). In addition, it is desirable to maintain stability in the absence of carrier proteins.

While it is widely appreciated that these possible protein instabilities can occur, until a protein has been studied it is impossible to predict the particular instability problems that a particular protein may have. Any of these instabilities can potentially result in the formation of a protein or protein by-product or derivative having lowered activity, increased toxicity, and/or increased immunogenicity. Indeed, protein precipitation can lead to thrombosis, non-homogeneity of dosage form and immune reactions. Thus, the safety and efficacy of any pharmaceutical formulation of a protein is directly related to its stability.

Accordingly, there continues to exist a need in the art for methods for improving protein stability during the concentration process as well as providing stability in the absence of other carrier proteins in a concentration sufficiently high for various routes of administration including, e.g., sub cutaneous injection, intra venous injection.

BRIEF SUMMARY OF THE INVENTION

One aspect of the present invention provides novel compositions and methods for obtaining concentrated preparations of IL-11, useful as bulk drug product.

Another aspect of the present invention provides compositions comprising formulations of IL-11 of a concentration, useful for administration in final dosage forms.

Preferred compositions include IL-11 and glycine, and optionally include a buffering agent. Preferred glycine concentrations range from 100 mM to 300 mM, with 300 mM most preferred. IL-11 concentration ranges from 0.1 mg/mL to 20.0 mg/mL, the most preferred being 5.0 mg/mL. Suitable buffering agents include histidine and sodium phosphate, ranging in concentration from 5 mM to 40 mM; with 10 mM preferred for sodium phosphate and 20 mM preferred for histidine, with sodium phosphate being the preferred buffering agent.

The compositions of the present invention may be either frozen, liquid, or lyophilized.

DETAILED DESCRIPTION OF THE INVENTION

In developing an appropriate drug dosage formulation, various factors are considered, including the solubility of a particular protein, its stability, and any particular handling requirements associated with the protein. While not all proteins are sensitive to handling, Applicants find that IL-11 is, in fact, sensitive to handling; both soluble aggregate and precipitate formation is observed after the protein has been "handled." Such handling includes, for example, any of the usual normal shear forces associated with shipping to clinical sites and with packaging operations. Also, sometimes protein formulations are pumped through stainless steel or other tubing during manufacture or stressed by the delivery systems which can subject them to shear forces; sometimes it is necessary to subject the protein to a variety of freeze/thaw cycles, thereby also exposing the protein to potential denaturations.

While some efforts have been undertaken to overcome the stability problem by lyophilizing the protein of interest and shipping the protein in lyophilized form, once the protein has reached its destination it must be reconstituted by either the health care worker or the patient. Proper reconstitution requires that the procedure be done under sterile conditions, that it be done gently, and that an assessment be made regarding the integrity of the reconstituted solution. Because of potential inconveniences associated with the use of lyophilized dosage forms, when possible, liquid dosage forms are more desirable. Development of stable liquid dosage forms of protein pharmaceuticals is a challenge, because generally the liquid form is less stable than the lyophilized form. However, if the stability problems of a liquid dosage form are overcome, the liquid form can be utilized.

Applicants find that some of the chemical instability of IL-11 is a result of hydrolysis between $Asp^{133}$ and $Pro^{134}$. Also, deamidation of $Asn^{49}$ to $Asp^{49}$ is detected. In addition, oxidation of $Met^{58}$ is observed. All of these chemical reactions are evidence of IL-11 protein chemical instability. IL-11 is also subject to certain physical instabilities including a dimerization process (which is actually a shift in equilibrium between the monomeric and dimeric forms of IL-11), as well as aggregate formation.

According to the present invention, the addition of glycine, at an appropriate pH, acts to prevent aggregation of IL-11 and protects IL-11 from the harmful effects of shearing. This in turn increases the ability to handle the protein and provides enhanced shelf-life for IL-11 products. The present invention also provides for IL-11 formulations, containing glycine, which are suitable for sub cutaneous injection. The IL-11 concentration ranges from 0.5 to 20.0 mg/mL. The IL-11 formulation can be in either a liquid or a lyophilized dosage form. Moreover, addition of an appropriate buffering agent slows the rate of hydrolysis, deamidation, and oxidation. Buffering is accomplished with a suitable buffer, or any buffering agent as is known to one skilled in the art, which will adequately buffer at neutral pH. Preferred is histidine; most preferred is sodium phosphate.

The following examples illustrate practice of the invention. These examples are for illustrative purposes only and are not intended in any way to limit the scope of the invention claimed. Example 1 describes the effects of various excipients on the shearing of IL-11. Example 2 relates to concentrating IL-11 solutions. Example 3 describes the thermal stability of IL-11 containing solutions. Example 4 relates to long-term IL-11 stability.

EXAMPLE 1

Resistance to Shear Effects

To examine the shear protecting effects of various excipients on the shearing of IL-11, IL-11 is added to solutions containing various buffers as set forth in Table I. Specifically, 2 mg/mL rhIL-11, in 20 mM sodium phosphate, 0.15 M NaCl, pH 7.0, is spiked into solutions containing various buffers and the solutions, at 0.1 mg/mL in 1-mL volume, are stirred vigorously at approximately 100 rpm using a triangular reacti-vial for 20 minutes. All samples are prepared in triplicate. Samples are centrifuged and the supernatant examined for protein concentration by Size-Exclusion High-Performance Liquid Chromatography (SEC-HPLC). Table I shows the effects of excipients on the recovery of rhIL-11.

Percent recovery is determined by examining samples before and after stirring. 100 μL aliquots are injected onto a TosoHaas TSK2000SW$_{XL}$ HPLC column (cat. #08540) using a buffer of 50 mM MES, 0.5 NaCl, pH 6.0, at a flow rate of 1 mL/min. Absorbance is monitored at 280 nm. A Waters HPLC system is used (Waters 600 multi-solvent delivery system, Waters 600E system controller, Waters WISP 712 auto-injector, Waters 490E programmable multi-wavelength detector and the Waters Expert HPLC software package). Percent recovery is determined by dividing the absorbance area of the rhIL-11 peak in the stirred sample by the absorbance area of the control sample. The recoveries of the three samples are averaged.

TABLE I

Excipient Effects on Shearing of rhIL-11

| Base Buffer | Additive[1] | pH | Percent Recovery |
|---|---|---|---|
| 50 mM sodium phosphate | 150 mM NaCl | 6.0 | 74 |
| | 1 M NaCl | 6.0 | 65 |
| 10 mM Histidine | 1 M NaCl | 7.5 | 63 |
| | 20 mM CaCl$_2$ | 7.5 | 89 |
| | 20 mM MgCl$_2$ | 7.5 | 89 |
| | 0.2 M glycine | 7.5 | 97 |
| | 0.5 M NaCl | 7.0 | 71 |
| | 0.2 M ethyl glycine | 7.0 | 98 |
| | 0.2 M BAPA | 7.0 | 77 |
| | 0.2 M GABA | 7.0 | 47 |
| | 0.2 M EACA | 7.0 | 84 |
| | 0.2 M DAVA | 7.0 | 63 |

[1]GABA = γ-amino-n-butyric acid
EACA = ε-amino-n-caproic acid
DAVA = δ-amino-n-valeric acid
BAPA = β-amino-n-propionic acid The greatest shear-protecting effects are observed with glycine, ethyl glycine, calcium chloride, and ε-amino-n-caproic acid.

EXAMPLE 2

Concentrating IL-11 Solutions

This example demonstrates the solubilizing effects of glycine. Samples are prepared to examine the effects of concentrating IL-11 solutions. Applicants find that stirred cell concentrating of IL-11, in the absence of glycine, leads to poor recoveries (85–90%) and can lead to increased levels of multimeric IL-11. The apparent molecular weights of these species, as determined using size-exclusion high-performance liquid chromatography, correspond to dimeric and trimeric forms.

An IL-11 containing solution (500 mL at 0.4 mg/mL) in 20 mM L-histidine, 0.25 M NaCl, pH 7.0, is concentrated to 5 mg/mL (40 mL) using a 100 mL stirred cell at 60 psi. As the volume decreases and the protein concentration increases, during the ultrafiltration step, the flow rate of solution through the YM10 (10 kD) molecular weight cutoff membrane decreases. This decrease in flow rate is due to a deposit of a layer of protein on the surface of the membrane. As the diafiltration step begins, and the glycine containing buffer is introduced (20 mM L-histidine, 0.3 M glycine, pH 7.0), the flow rate increases. This increase in flow rate is indicative of a solubilization of the layer of protein deposited on the membrane surface. Thus, utilizing glycine increases IL-11 recoveries from 85–90% to 98–100%.

EXAMPLE 3

Thermal Stability of IL-11

This example demonstrates that the addition of glycine increases the temperature to which IL-11 will remain soluble.

Thermal denaturation of IL-11 containing solutions is performed using an SLM/Aminco 800C. fluorescence spectrophotometer. As IL-11 denatures in solution, it precipitates. Based on this observation, a fluorescence spectrophotometer is used to monitor right-angle light-scattering by exciting the sample at 320 nm, and monitoring emission also at 320 nm. The emission signal is monitored continuously as the temperature of the cuvette is raised at a rate of 1° C./minute. Temperature is controlled using a Neslab 110C. gradient controlled waterbath. The temperature at which 50% of the protein is precipitated is described as the precipitation temperature ($T_p$).

Solutions containing various amounts of IL-11 were thermally denatured. As the protein concentration increases, in general the $T_p$ decreases as the precipitation event is protein concentration dependent. Two solutions of IL-11 are examined: PBS (50 mM sodium phosphate, 150 mM NaCl, pH 7.0) and a glycine containing solution of 20 mM L-histidine, 300 mM glycine, pH 7.0. Table II demonstrates that as the protein concentration increases, the $T_p$ decreases dramatically in the PBS solution, but not in the glycine containing solution. The data demonstrates that glycine helps to stabilize IL-11 in solution.

TABLE II

Effect of IL-11 Concentration on Precipitation Temperature

| IL-11 Concentration (mg/mL) | 50 mM sodium phosphate, 150 mM NaCl, pH 7.0 | 20 mM L-histidine, 300 mM glycine, pH 7.0 |
|---|---|---|
| 0.1 | 88.5° C. | >96.0° C. |
| 0.5 | 80.0° C. | >96.0° C. |
| 1.0 | 75.0° C. | >96.0° C. |
| 2.5 | 70.0° C. | 95.0° C. |
| 5.0 | 66.0° C. | 94.0° C. |

EXAMPLE 4

Long-term IL-11 Stability

To assess longer term effects of glycine on IL-11 stability, IL-11 is incubated for up to 12 months, at different temperatures, in the presence of 10 mM sodium phosphate containing either 150 mM or 300 mM glycine. The data clearly demonstrate that the addition of more glycine aids in increasing the shelf-life stability of this protein in the liquid state, at elevated temperatures. Further, the absence of glycine altogether leads to a dramatic loss of rhIL-11 at elevated temperatures. rhIL-11 is prepared, at 5.0 mg/mL in two formulations: 10 mM sodium phosphate, 300 mM glycine, pH 7.0 and 10 mM sodium phosphate, 150 mM glycine, pH 7.0. One mL samples are prepared in 2-mL molded vials (Kimble), stoppered and crimped, and incubated at six temperatures for up to 12 months (−80° C., −20° C., 2–8° C., 30° C., 40° C., 50° C.). Protein recoveries are determined a reversed-phase HPLC method and the results are shown in Table III.

TABLE III

Effect of Glycine Concentration on Percent rhIL-11 Recoveries at Different Temperatures

| INCUBATION TEMPERATURE | 10 mM sodium phosphate 300 mM glycine, pH 7.0 | 10 mM sodium phosphate 150 mM glycine, pH 7.0 |
|---|---|---|
| −80° C. at 12 months | 100 | 100 |
| −20° C. at 12 months | 96.9 | 97.2 |
| 2–8° C. at 12 months | 98.3 | 100 |
| 30° C. at 12 months | 91.5 | 71.7 |
| 40° C. at 6 months | 72.4 | 63.2 |
| 50° C. at 2 months | 72.9 | 75.5 |

Another set of samples is prepared in a formulation of 10 mM sodium phosphate, 300 mM glycine, pH 7.0. These samples are liquid and stored at 2–8° C. for up to 18 months. The samples retain IL-11 activity.

Another set of samples is prepared in a formulation of 20 mM L-histidine, 300 mM glycine, pH 7.0. These samples are lyophilized and stored at 2–8° C. for up to 18 months. The samples retain IL-11 activity.

While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and, consequently, only such limitations as appear in the appended claims should be placed thereon. Accordingly, it is intended in the appended claims to cover all such equivalent variations which come within the scope of the invention as claimed.

What is claimed is:

1. A composition comprising IL-11 and glycine.
2. The composition of claim 1, where the amount of said glycine ranges from 50 to 600 mM.
3. The composition of claim 1, where the amount of said glycine is about 300 mM.
4. The composition of claim 1, where the amount of said glycine is about 150 mM.
5. The composition of claim 1, where the amount of said IL-11 is about 0.1 to 20 mg/mL.
6. The composition of claim 1, where the amount of said IL-11 is about 5.0 mg/mL.
7. The composition of claim 1, where the amount of said IL-11 is about 5.0 mg/mL and said glycine is about 300 mM.
8. A composition comprising IL-11, glycine, and a buffering agent.
9. The composition of claim 8, where said buffering agent is a member selected from the group consisting of histidine and phosphate.
10. The composition of claim 9, where said buffering agent is sodium phosphate.
11. The composition of claim 9, where the amount of said phosphate ranges from about 5 mM to 20 mM.
12. The composition of claim 10, where the amount of said phosphate is about 10 mM.
13. The composition of claim 9, where the amount of said histidine ranges from about 5 mM to 40 mM.
14. The composition of claim 11, where the amount of said histidine is about 20 mM.
15. A composition comprising about 5.0 mg/mL IL-11, 300 mM glycine, and 10 mM sodium phosphate.
16. A composition comprising about 5.0 mg/mL IL-11, 300 mM glycine, and 20 mM histidine.
17. A composition comprising des-Pro-IL-11 and glycine.
18. The composition of claim 17 where the amount of said des-Pro-IL-11 is about 0.1 to 20 mg/mL.
19. The composition of claim 17 where the amount of said glycine is about 50 to 600 mM.
20. A composition comprising about 5.0 mg/mL des-Pro-IL-11 and 300 mM glycine.

* * * * *